US012564701B2

(12) United States Patent
Farrissey et al.

(10) Patent No.: US 12,564,701 B2
(45) Date of Patent: Mar. 3, 2026

(54) TUBE HAVING AN INTERIOR LUBRICIOUS COATING AND SYSTEMS AND METHODS OF APPLYING THE SAME

(71) Applicants:Crannmed Limited, County Galway (IE); TECHNOLOGICAL UNIVERSITY DUBLIN, Dublin (IE)

(72) Inventors: Liam Farrissey, County Galway (IE); Brendan Duffy, County Kildare (IE); Sankalp Agarwal, Dublin (IE)

(73) Assignees: Crannmed Limited, County Galway (IE); Technological University Dublin, Dublin (IE)

( * ) Notice: Subject to any disclaimer, the term of this patent is extended or adjusted under 35 U.S.C. 154(b) by 441 days.

(21) Appl. No.: 17/415,128

(22) PCT Filed: Dec. 21, 2019

(86) PCT No.: PCT/IB2019/001412
§ 371 (c)(1),
(2) Date: Jun. 17, 2021

(87) PCT Pub. No.: WO2020/128632
PCT Pub. Date: Jun. 25, 2020

(65) Prior Publication Data
US 2022/0047843 A1     Feb. 17, 2022

Related U.S. Application Data

(60) Provisional application No. 62/874,161, filed on Jul. 15, 2019, provisional application No. 62/857,528, (Continued)

(51) Int. Cl.
*A61M 25/00*     (2006.01)
*A61M 25/10*     (2013.01)
(Continued)

(52) U.S. Cl.
CPC .... *A61M 25/0009* (2013.01); *A61M 25/0045* (2013.01); *A61M 25/1006* (2013.01);
(Continued)

(58) Field of Classification Search
CPC .......... A61M 25/0009; A61M 25/0045; A61M 25/1006; A61M 25/1031; A61M 25/1034;
(Continued)

(56) References Cited

U.S. PATENT DOCUMENTS 5,089,297 A * 2/1992 Koga ..................... F16L 55/164
427/388.1
5,212,000 A * 5/1993 Rose .................. B01D 67/0088
428/34.7
(Continued)

FOREIGN PATENT DOCUMENTS

| CN | 105398030 | * | 3/2016 |
| CN | 105398030 B | | 10/2017 |
| EP | 2231381 B1 | | 9/2008 |

OTHER PUBLICATIONS

European Search Report for related European Patent Application No. 19861266.5 dated Jul. 12, 2023, 12 pages.
(Continued)

*Primary Examiner* — Brian K Talbot
(74) *Attorney, Agent, or Firm* — Morgan, Lewis & Bockius LLP

(57) ABSTRACT

A method for coating an inner lumen surface of a tube with a coating solution comprises the steps of moving a coating solution through a tube via a withdrawal system and depositing the coating solution onto an inner lumen surface of the tube. The thickness of the coating solution is deposited onto the inner lumen surface of the tube is between 1 μm and 25 μm. The method further comprises applying a pressure to the tube using a pressure source when the coating solution is
(Continued)

Meniscus Profile

101

Pressure Applied within the tube to manipulate a surface tension between the coating solution and the inner lumen surface of the tube.

23 Claims, 6 Drawing Sheets

Related U.S. Application Data filed on Jun. 5, 2019, provisional application No. 62/783,821, filed on Dec. 21, 2018.

(51) Int. Cl.
    *B05D 3/10*          (2006.01)
    *B05D 7/22*          (2006.01)
(52) U.S. Cl.
    CPC . *A61M 25/1034* (2013.01); *A61M 2025/0042* (2013.01); *A61M 2025/1061* (2013.01); *A61M 2205/0222* (2013.01); *A61M 2205/0238* (2013.01); *B05D 3/10* (2013.01); *B05D 7/22* (2013.01); *B05D 7/225* (2013.01); *B05D 2254/04* (2013.01)
(58) Field of Classification Search
    CPC . B05D 3/10; B05D 7/22; B05D 7/225; B05D 2254/04
    USPC .......................................... 427/2.3, 230, 238
    See application file for complete search history.

(56)                References Cited

U.S. PATENT DOCUMENTS

| | | | | | | |
|---|---|---|---|---|---|---|
| 5,603,991 | A | * | 2/1997 | Kupiecki | .......... | A61M 25/0009 |
| | | | | | | 427/430.1 |
| 5,667,841 | A | * | 9/1997 | Toyoda | ............... | F16L 55/1645 |
| | | | | | | 427/295 |
| 6,024,693 | A | * | 2/2000 | Schock | ............... | A61M 60/515 |
| | | | | | | 600/18 |
| 6,706,025 | B2 | * | 3/2004 | Engelson | ................ | A61L 29/14 |
| | | | | | | 604/265 |
| 7,060,051 | B2 | * | 6/2006 | Palasis | .............. | A61M 25/1027 |
| | | | | | | 604/101.01 |
| 7,112,298 | B2 | * | 9/2006 | Kampa | ................... | A61L 29/12 |
| | | | | | | 264/306 |
| 8,343,579 | B2 | * | 1/2013 | Gillanders | .......... | C09D 163/00 |
| | | | | | | 427/238 |
| 9,585,780 | B2 | * | 3/2017 | Pacetti | .................... | A61F 2/915 |
| 10,155,599 | B2 | * | 12/2018 | Pacetti | .................... | A61L 31/14 |
| 2004/0086542 | A1 | * | 5/2004 | Hossainy | ................ | A61L 31/16 |
| | | | | | | 427/2.28 |
| 2005/0238829 | A1 | | 10/2005 | Motherwell et al. | | |
| 2005/0288774 | A1 | | 12/2005 | Case et al. | | |
| 2009/0208175 | A1 | * | 8/2009 | Hongo | ................... | G02B 6/032 |
| | | | | | | 428/34.1 |
| 2011/0029069 | A1 | * | 2/2011 | Kim | ....................... | A61L 27/507 |
| | | | | | | 623/1.46 |
| 2011/0274835 | A1 | * | 11/2011 | Liu | .......................... | B05D 7/22 |
| | | | | | | 427/238 |
| 2012/0165922 | A1 | * | 6/2012 | Gong | ..................... | B05D 3/107 |
| | | | | | | 623/1.42 |
| 2012/0216905 | A1 | * | 8/2012 | Pacetti | .................... | A61L 31/16 |
| | | | | | | 141/1 |
| 2012/0216908 | A1 | * | 8/2012 | Pacetti | .................... | A61L 31/10 |
| | | | | | | 141/2 |
| 2012/0216913 | A1 | * | 8/2012 | Pacetti | ...................... | A61F 2/86 |
| | | | | | | 141/18 |
| 2012/0216914 | A1 | * | 8/2012 | Pacetti | .................. | B65B 31/044 |
| | | | | | | 141/65 |
| 2012/0216916 | A1 | * | 8/2012 | Pacetti | .................... | A61F 2/915 |
| | | | | | | 141/98 |
| 2013/0206667 | A1 | * | 8/2013 | Steinecker | ............. | B05D 7/222 |
| | | | | | | 210/198.2 |
| 2015/0297800 | A1 | * | 10/2015 | Weikart | .................... | A61J 1/05 |
| | | | | | | 422/430 |

OTHER PUBLICATIONS

International Search Report and Written Opinion dated Jul. 31, 2020 for International Patent Application No. PCT/IB2019/001412, 19 pages.
First Chinese Office Action dated May 27, 2022 for Chinese Patent Application No. 201980084541.8, 13 pages with translation.
International Preliminary Report on Patentability dated Jul. 1, 2021 for International Patent Application No. PCT/IB2019/001412, 16 pages.

* cited by examiner

200

TUBE HAVING AN INTERIOR LUBRICIOUS COATING AND SYSTEMS AND METHODS OF APPLYING THE SAME

CROSS REFERENCE TO RELATED APPLICATIONS

This application is a U.S National Phase of International Application No. PCT/IB2019/001412 filed on Dec. 21, 2019, which claims the benefit of U.S. Provisional Patent Application No. 62/783,821 filed Dec. 21, 2018 entitled "A Tube Having An Interior Lubricious Coating and Systems and Methods of Applying the Same", U.S. Provisional Patent Application No. 62/857,528 filed Jun. 5, 2019 entitled "Balloon-Occluded Transarterial Chemoembolization Device", and U.S. Provisional Patent Application No. 62/874,161 filed Jul. 15, 2019 entitled "Balloon Occlusion Microcatheter", each of which is incorporated by reference herein in their entirety.

FIELD OF THE INVENTION

The present invention generally relates to a tube having an interior lubricious coating and systems and methods of applying the same, and more particularly in some embodiments, to a device, system and methods of applying lubricious coating on the inner surface of medical device catheters.

BACKGROUND OF THE INVENTION

Lubricious coatings for medical device tubes and catheters may be used in order to enhance the performance of the tubes such that other devices that pass through the lumen of the tube will pass with reduced friction and resistance and higher performance.

Current state of the art coatings typically consist of the use of low friction materials typically PTFE, FEP and HDPE's. Certain specialized coatings exist, however they must be applied to the surface while the material is in a flat state rather than luminal state or a vertical state.

Typical applications in the field of medical device technology may include, for example, delivery catheters whereby a larger bore catheter would facilitate the passage of one or multiple smaller catheters through its lumen to a desired anatomical location via the human vasculature system. Lubricious properties in such application are a significant advantage in the use of these devices affecting a clinical outcome.

Further, coatings applied to materials to enhance lubricity are typically applied to the outer surface of catheters, tubing and wiring. However, to date, hydrophobic or hydrophilic coatings that can be applied viably to the surface of the inner lumen of medical device tubing are not commonly known.

BRIEF SUMMARY OF THE INVENTION

In one embodiment, there is a method for coating an inner lumen surface of a tube with a coating solution including the steps of moving a coating solution through a tube via a withdrawal system and depositing the coating solution onto an inner lumen surface of the tube, wherein a thickness of the coating solution being deposited onto the inner lumen surface of the tube is between 1 μm and 25 μm and applying a pressure to the tube using a pressure source when the coating solution is within the tube to manipulate a surface tension between the coating solution and the inner lumen surface of the tube.

In one embodiment, the method further includes preparing the inner lumen surface of the tube for application of the coating solution using a cleaning solution. The cleaning solution may be saline or an equivalent. The inner lumen surface may be pre-treated with one or more of silanes, plasma, or corona plasma discharge, the one or more of silanes, plasma, or corona plasma acting as an adhesion promoters In one embodiment, a ratio between an inner diameter of the tube and a length of the tube is between 1:100 and 1:4000.

In one embodiment, the withdrawal system includes a syringe and plunger. The withdrawal system may include a pump.

In one embodiment, the pressure being applied to the tube is positive pressure. In one embodiment, the pressure being applied to the tube is negative pressure. In one embodiment, the method further includes curing the coating solution such that it adheres to the inner lumen surface of the tube. The coating solution may be heat cured between 20 degrees Celsius and 90 degrees Celsius. The coating solution may be heat cured for a duration of between 10 minutes and 8 hours. The coating solution may be cured using ultraviolet light.

In one embodiment, the coating solution is a hydrophilic coating. In one embodiment, the coating solution is a hydrophobic coating. In one embodiment, the coating solution is diluted with a dilution solution by varying the concentration of the dilution solution to change the thickness of the coating solution.

In one embodiment, the method includes applying a primer solution or a basecoat solution between the inner lumen surface of the tube and the coating solution, wherein the primer solution or the basecoat solution is used as an adhesion promoter.

In one embodiment, the method includes simultaneously applying the coating solution to the inner lumen surface of the tube and an outer surface of the tube. Multiple inner lumens of multiple tubes may be coated simultaneously.

Another method of the present invention provides a method for coating an inner lumen surface of a tube with a coating solution comprising the steps of moving a coating solution through a tube via a withdrawal system and depositing the coating solution onto an inner lumen surface of the tube, wherein a thickness of the coating solution being deposited onto the inner lumen surface of the tube is between 1 μm and 25 μm, wherein the withdrawal system includes a pump. The method further includes applying a positive pressure to the tube using a pressure source when the coating solution is within the tube to manipulate a surface tension between the coating solution and the inner lumen surface of the tube, and curing the coating solution such that it adheres to the inner lumen surface of the tube, wherein the coating solution is heat cured between 20 degrees Celsius and 90 degrees Celsius.

Another embodiment of the present invention provides a system for coating an inner lumen surface of a tube including a syringe having a plunger, the syringe containing a coating solution, and a motor coupled to the plunger, the motor configured to push the plunger to cause the coating solution to withdraw from the syringe and deposit onto the inner lumen surface of the tube, wherein a thickness of the coating solution being deposited onto the inner lumen surface of the tube is between 1 μm and 25 μm.

In one embodiment, the system further comprises a pressure source coupled to the inner lumen surface of the tube. The pressure source may generate positive pressure, the positive pressure being applied when the coating solution is withdrawn and configured to manipulate a surface tension between the coating solution and the inner lumen surface of the tube. The positive pressure may be created using one or more of an argon, carbon, hydrogen, oxygen, nitrogen, and air. The positive pressure generated by the pressure source may be constant and applied in the same direction as the coating solution is being withdrawn into the syringe. The positive pressure may be variable and varied in accordance with the distance between a meniscus of the coating solution in the tube and the pressure source.

In one embodiment, the tube has a first end and a second end, and a seal attached to one of the first end or the second end, the seal being disposed between the tube and the syringe.

Another embodiment of the present invention provides a tube for insertion into the body, the tube having an inner lumen surface, and a coating solution deposited on the inner lumen surface, the coating solution having a thickness between 1 µm and 25 µm, wherein the tube is configured to receive an object and the coating solution deposited on the inner lumen surface of the tube is configured to reduce the friction between the inner lumen surface and the object, and wherein a coefficient of friction of the inner lumen surface of the tube between 0.3 and 0.01.

In one embodiment, the tube includes an expandable portion configured to expand a diameter of the tube upon receiving the object. The expandable portion may be configured to unfold to expand the diameter of the tube upon receiving the object and configured to fold when the object is no longer in the tube. The expandable portion may be configured to stretch such that the tube increases its diameter upon receiving the object and configured to retract when the object is no longer in the tube.

In one embodiment, the tube includes an outer tube disposed partially around the tube. The tube may also include a balloon having a proximal end and a distal end, the distal end being coupled to the tube, wherein in an inflated state the tube is partially disposed within the balloon.

In one embodiment, the tube includes an opening configured to engage the object, wherein the tube is configured to aspirate the object through the opening such that the object interacts with the coating solution to increase the ease aspiration and reduce friction between the object and the inner lumen surface.

In one embodiment, the tube includes at least one tapered portion, the at least one tapered portion being located at a distal end of the tube.

In one embodiment, the tube is sized and shaped for the delivery of compressible embolic particles ranging in size between 75 µm to 1 mm such that the coating solution deposited on the inner lumen surface assists with the delivery of the compressible embolic particles and reduces blockage that occurs due to buildup of friction between the compressible embolic particles and the inner lumen surface.

In one embodiment, the coating solution is configured to reduce friction between the inner lumen surface and particles injected into the tube so that injection of the particles through the tube is able to be paused and restarted with minimal re-activation force or effort.

In one embodiment, the coating solution has a thickness between 1 µm and 20 µm. The coating may be biocompatible, hydrophilic, or hydrophobic.

In one embodiment, the coefficient of friction of the inner lumen surface of the tube is between about 0.01 and about 0.3.

In one embodiment, a coefficient of friction of the inner lumen surface of the tube is decreased by between 50% and 500% as compared to a coefficient of friction of the inner lumen surface of a tube without the coating solution deposited on the inner lumen surface.

In one embodiment, a slip resistance index of the inner lumen surface of the tube is less than or equal to about 0.3.

In one embodiment, a slip resistance index of the inner lumen surface of the tube is decreased by between 50% and 500% as compared to a slip resistance index of the inner lumen surface of a tube without the coating solution deposited on the inner lumen surface.

BRIEF DESCRIPTION OF THE SEVERAL VIEWS OF THE DRAWINGS

The foregoing summary, as well as the following detailed description of embodiments of a tube having an interior lubricious coating and systems and methods of applying the same, will be better understood when read in conjunction with the appended drawings of exemplary embodiments. It should be understood, however, that the invention is not limited to the precise arrangements and instrumentalities shown.

DETAILED DESCRIPTION OF EXEMPLARY EMBODIMENTS OF THE INVENTION

Figure 1:
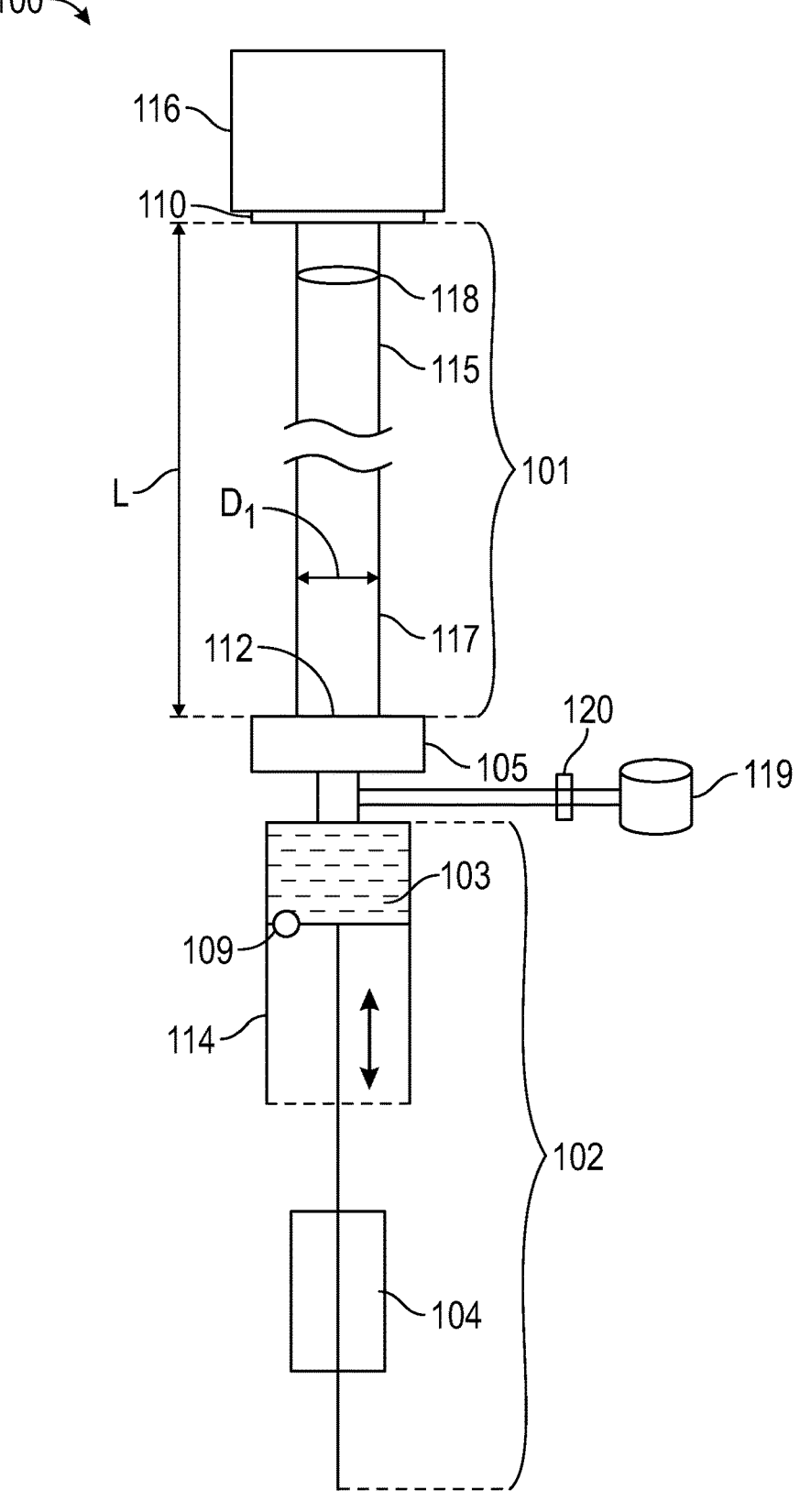
FIG. 1 is an illustration of an exemplary tube coating system in accordance with an exemplary embodiment of the present invention.

Methods and systems for modifying a surface are needed in many different applications, including applications in the medical, biotechnology, pharmaceutical and other life sciences industries. Typically, applications in these industries utilize materials, such as tubing, manufactured or fabricated from a polymer, glass, silicon, metal, or other inorganic or organic material. However, the surfaces of these materials can have undesirable properties. The luminal surface of tubing configured to receive an object or material therethrough (e.g., embolic particles, clots, tumors, accessory devices, catheters, medicaments, coils, tools, or devices) can be rough and/or non-biocompatible, and the original surface can require modification, such as a coating, to reduce the friction and/or be biocompatible. For example, coating the inner luminal surface of a catheter can reduce the likelihood that a clot breaks within the catheter, and can improve the aspiration of the entire clot into the catheter. This in turn can reduce the likelihood of adverse effects (e.g., pulmonary embolisms) which occur when clots breaks loose and travel through the bloodstream (e.g., to the lungs).

Preferably, such modifications should be stable for the desired use or multiple uses. Furthermore, if such modifications are to be incorporated into a device or apparatus, then such modifications are preferably amenable to efficient, cost-effective and reproducible production. The present disclosure provides methods and systems for applying coatings, and exemplary applications in which reduced friction and/or biocompatible coatings are useful including catheters, expandable sheaths, tapered sheaths, and others.

While preferred embodiments of the subject matter disclosed herein have been shown and described, it will be obvious to those skilled in the art that such embodiments are provided by way of example only. Numerous variations, changes, and substitutions will now occur to those skilled in the art without departing from the subject matter disclosed herein. It should be understood that various alternatives to the embodiments of the subject matter disclosed herein may be employed in practicing the subject matter disclosed herein. It is intended that the following claims define the scope of the subject matter disclosed herein and that methods and structures within the scope of these claims and their equivalents be covered thereby.

DEFINITIONS

The term "coating", as used herein, can refer to a freely flowing composition or mixture that is employed to coat a surface of a tube. Coating can refer to any means of modifying at least a portion of an exposed surface with another material. As described herein, the interactions between the original surface and the coating material can include hydrophobic interactions, covalent interactions, electrostatic interactions, hydrogen-bond interactions, non-covalent interactions as well as any combination of these interactions. As a result of such a coating, the properties of the new surface differ from the properties of the original surface. In certain embodiments, a coating, such as a lubricant, can be used to reduce static and/or kinetic friction to ease the contact of two different surfaces.

The term "layer" as used herein can refer to a coating or material covering a surface or forming an overlying part or segment. Two different layers may have overlapping portions whereby material from one layer may be in contact with material from another layer. Contact between materials of different layers can be measured by determining a distance between the materials. For example, Raman spectroscopy, ellipsometry, phase contrast, and dark field microscopy may be employed in identifying materials from two layers present in close proximity to each other.

The term "biocompatible", as used herein, can refer to a surface of a tube which causes no reaction or a minimal or below threshold reaction when it comes into contact with a human or animal body or its blood, fluids or other biological membranes. The term "biocompatible", as used herein, can also refer to a synthetic or natural material used to replace part of a living system or to function in intimate contact with living tissue. Biocompatible materials are chemically inert, non-toxic, substantially non-immunogenic and non-thrombogenic.

The terms "bioabsorbable," "biodegradable," "bioerodible," "bioresorbable," and "resorbable" are terms recognized by those having skill in the art, and can be used synonymously. Bioabsorbable polymers typically differ from non-bioabsorbable polymers or "durable" polymers in that the former can be absorbed (e.g., degraded) during use. In certain embodiments, such use involves in vivo use, such as in vivo therapy, and in other certain embodiments, such use involves in vitro use. In general, degradation attributable to biodegradability involves the degradation of a bioabsorbable polymer into its component subunits, or digestion, e.g., by a biochemical process, of the polymer into smaller, non-polymeric subunits. In certain embodiments, biodegradation can occur by enzymatic mediation, degradation in the presence of water (hydrolysis) and/or other chemical species in the body, or both. The bioabsorbability of a polymer can be shown in-vitro as described herein or by methods known to one of skill in the art. An in-vitro test for bioabsorbability of a polymer does not require living cells or other biologic materials to show bioabsorption properties (e.g. degradation, digestion).

The term "about" or "approximately" can refer to an acceptable error range for the particular value as determined by one of ordinary skill in the art, which will depend in part on how the value is measured or determined, e.g., the limitations of the measurement system. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

Methods & Systems for Making a Tube having an Interior Lubricious Coating

Exemplary embodiments of the present invention provide a tube having a coating solution on the inner lumen surface of tube 101 and systems and methods of applying the same. An exemplary embodiment is shown in FIGS. 1-6. In use, tube coating system 100 may be used to deliver a thin coating of solution to the inner lumen surface of a tube or catheter during a coating process. Specifically, the coating solution may be used to lubricate the inner lumen of a tube or catheter for the introduction of instruments within the inner lumen.

Referring to FIG. 1, tube coating system 100 may include tube or catheter 101, withdrawal system 102, and seal 105. Tube 101 may be coupled to withdrawal system 102 via seal 105. Tube 101 may be configured to be coated with coating solution 103. Tube 101 may include inner lumen 115 having an inner lumen surface 117, outer surface 118, first end 110 and second end 112. Tube 101 may include inner diameter $D_1$. The ratio between inner diameter $D_1$ of tube 101 and length L of tube 101 may be between 1:100 and 1:4000. Tube 101 may be any length desired. For example, tube 101 may be between 20 cm and 2 m, 30 cm to 1.5 m, 40 cm to 1 m, or tube 101 may be 0.5 m, 1 m, 1.5 m, 2 m, greater than 2 m, or less than 20 cm.

In some embodiments, tube 101 may be sized and shaped for the delivery of clots, tumors, particles, accessory devices, catheters, medicaments, coils, tools, or devices. For example, tube 101 may be sized and shaped for the delivery of compressible embolic particles ranging in size between 75 μm to 1 mm. Coating solution 103 may be deposited on inner lumen surface 117 such that coating solution 103 assists with the delivery of the compressible embolic particles and reduces blockage that occurs due to buildup of friction between the compressible embolic particles and inner lumen surface 117.

In one embodiment, tube 101 is cylindrical and is comprised of Pebax. Such examples include PEBAX 7233, PEBAX 7033, PEBAX 6333, PEBAX 4033, PEBAX 3533, PEBAX 2533, PEBAX 5533, etc. However, tube 101 may be any shape and may be comprised of nylon, polyether, or polyurethane. The nylon may include any suitable nylon including, for example, any nylon suitable for use in medical devices. In certain embodiments, the nylon may be selected from the group of Nylon-6, Nylon-7, Nylon-8, Nylon-9, Nylon-10, Nylon-1 1, Nylon-12, Nylon-13, Nylon-14, Nylon-15, Nylon-16, Nylon-17, Nylon-18, Nylon-6,6, Nylon-6,8, Nylon-6, 10, Nylon-6, 12, Nylon-6, 14, Nylon-8,8, Nylon-8, 10, Nylon-8, 12, Nylon-8, 14, Nylon-10, 10, Nylon-10, 12, Nylon-8, 12, Nylon-10, 14, Nylon-12, 12, Nylon-12, 14, Nylon-14, 16, and combinations thereof. In certain embodiments, the nylon may be selected from the group of Nylon-6, Nylon-11, Nylon-12, Nylon-6, 6, Nylon-6, 10, and combinations thereof. The nylon can be copolymerized with other polymers, such as polyether, for example. Block copolymers of the nylons such as polyether-co-Nylon-12 can be used if desired. Other examples of nylon-including polymers that are within the scope of "nylon" as used herein, include polyurethane-block-nylon, polyester-block-nylon, and poly siloxane-block-nylon.

As an alternative to polyamide elastomers, it is also possible to utilize polyester/polyether segmented block copolymers and obtain similar properties. Such polymers are made up of at least two polyester and at least two polyether segments. The polyether segments are the same as previously described for the polyamide/polyether block copolymers useful in the invention. The polyester segments are polyesters of an aromatic dicarboxylic acid and a two to four carbon diol. Suitable dicarboxylic acids used to prepare the polyester segments of the polyester/polyether block copolymers are ortho-, meta- or para-phthalic acid, napthalenedicarboxylic acid or meta-terphenyl-4,4'-dicarboxylic acids. It is contemplated that the composition of tube 101 may be selected based on the application (e.g., an application requiring more or less tube flexibility), optimizing adherence of the coating solution to inner lumen surface 117 of tube 101, reducing friction between inner lumen surface 117 and an object (e.g., a clot) drawn into tube 101, and/or preventing breakage of an object as it is drawn into tube 101.

In certain embodiments, coating solution 103 is applied to a surface (e.g., an inner lumen surface of a tube or catheter) to reduce friction between the surface and an object (such as a clot, a tumor, particles, accessory devices, catheters, medicaments, coils, tools, or devices) drawn into tube 101. In certain embodiments, the friction between a surface coated with coating solution 103 and an object is reduced by at least about 10%, at least about 20%, at least about 30%, at least about 40%, at least about 50%, at least about 60%, at least about 70%, at least about 80%, at least about 90%, or at least about 95% as compared to the friction between an uncoated surface and an object drawn into tube 101. In some embodiments, the friction between a surface coated with coating solution 103 and an object is reduced by greater than 100% as compared to the friction between an uncoated surface and an object drawn into tube 101. For example, the friction between a surface coated with coating solution 103 and an object may be reduced by at least about 100%, at least about 200%, at least about 300%, at least about 400%, at least about 500%, or greater than 500% as compared to the friction between an uncoated surface and an object drawn into tube 101. In some embodiments, the friction between a surface coated with coating solution 103 and an object may be reduced between 2 fold and 100 fold compared to the friction between an uncoated surface and an object. For example, the friction between a surface coated with coating solution 103 and an object may be reduced by 10 fold compared to the friction between an uncoated surface and an object. In some embodiments, coating solution 103 is configured to reduce friction between inner lumen surface 117 and particles and/or objects injected into tube 101 so that the injection of the particles through tube 101 may be paused and restarted with minimal re-activation force or effort Tube 101 may have a surface (e.g., inner lumen surface 117) with a low coefficient of friction. Any description herein of the coefficient of friction may refer to a static coefficient of friction, or a dynamic coefficient of friction. Any of the coefficient of friction values described herein may be for a static coefficient of friction value, or for a dynamic coefficient of friction value. For example, when inner lumen surface 117 of tube 101, having coating solution 103, contacts an object, the coefficient of friction may be less than or equal to about 0.2, less than or equal to 0.175, less than or equal to 0.15, less than or equal to 0.125, less than or equal to 0.10, less than or equal to 0.075, less than or equal to 0.05, or less than or equal to 0.01. In some instances, the coefficient of friction may fall between any of the values described above, such as between 0.05 and 0.075, or 0.10 and 0.05, or 0.10 and 0.075. The coefficient of friction of tube 101 may be less than that of an uncoated tube. When inner lumen surface 117 of tube 101 not having coating solution 103 contacts an object, the coefficient of friction may be greater than or equal to 0.05, greater than or equal to 0.0.75, greater than or equal to 0.10, greater than or equal to 0.125, greater than or equal to 0.15, greater than or equal to 0.175, or greater than or equal to 0.2. In some embodiments, coating solution 103 has a coefficient of friction less than that of PTFE. For example, coating solution 103 may have a coefficient of friction less than 0.1. In some embodiments, the coefficient of friction of coating solution 103 may be less than about 0.3 when coating solution 103 is hydrated. The coefficient of friction value may be determined using an American Society of Testing and Materials (ASTM) approved protocol.

In some instances, a surface of tube 101 coated with coating solution 103 may have a low slip resistance index as compared to an uncoated surface. In some instances, the coated surface may have a slip resistance index less than or equal to about 0.6, less than or equal to about 0.55, less than or equal to about 0.50, less than or equal to about 0.45, less than or equal to about 0.40, less than or equal to about 0.35, less than or equal to about 0.30, less than or equal to about 0.25, less than or equal to about 0.20, less than or equal to about 0.15, less than or equal to about 0.10, or less than or equal to about 0.05. In some instances, the uncoated surface may have a slip resistance index greater than or equal to about 0.2, greater than or equal to about 0.25, greater than or equal to about 0.30, greater than or equal to about 0.35, greater than or equal to about 0.40, greater than or equal to about 0.45, greater than or equal to about 0.50, greater than or equal to about 0.55, greater than or equal to about 0.60, greater than or equal to about 0.70, greater than or equal to about 0.80, or greater than or equal to about 0.90.

In certain embodiments, coating solution 103 applied to a surface (e.g., inner lumen surface 117 of tube or catheter 101) to reduce the slip resistance index of a surface such that an object may be more easily drawn into tube 101 and without breakage of the object. In some embodiments, coating solution 103 may aid the passage of a device or catheter through tube 101 t coated with coating solution 103. In certain embodiments, the slip resistance index of a surface coated with coating solution 103 is decreased by at least about 10%, at least about 20%, at least about 30%, at least about 40%, at least about 50%, at least about 60%, at least about 70%, at least about 80%, at least about 90%, or at least about 95% as compared to the slip resistance index of an uncoated surface. In some embodiments, the slip resistance index of a surface coated with coating solution 103 is decreased by greater than 100% as compared to the slip resistance index of an uncoated surface. For example, the slip resistance index of a surface coated with coating solution 103 may be decreased by at least about 100%, at least about 200%, at least about 300%, at least about 400%, at least about 500%, or greater than 500% as compared to the slip resistance index of an uncoated surface.

In certain embodiments, coating a surface of tube 101 with coating solution 103 may improve aspiration effectiveness of an object into tube 101. Reducing the resistance for clot being aspirated into tube 101 may help to take more of the clot from the vasculature in one pass, and additionally reduces the potential for the clot to break up and migrate further into the body. Tube 101 having inner lumen surface 117 coated with coating solution 103 may be designed to aspirate an object into tube 101 when tube 101 is oriented 90 degrees to a maximum cross-sectional plane of the object, or any other angle including but not limited to greater than, less than, or equal to about 85 degrees, 80 degrees, 75 degrees, 70 degrees, 65 degrees, 60 degrees, 50 degrees, 40 degrees, 30 degrees, 20 degrees, 10 degrees, 5 degrees, or 0 degrees to a maximum cross-sectional plane of the object.

Tube 101 may be formed from a single integral piece. Tube 101 may be a unitary construct and/or may be a single molded/shaped piece. In some instances, tube 101 may be one piece without having additional pieces used to form tube 101. In alternative embodiments, tube 101 need not be a unitary construct. A plurality of portions may be provided to form tube 101. For example, an end of tube 101 may be formed of one piece (e.g., a flared end for aspirating larger objects) and the remainder of tube 101 formed of another piece. The separate portions can or cannot be releasably connected to one another. The separate portions can or cannot be permanently affixed to one another. The separate portions can have the same material properties or different material properties. In some embodiments, tube 101 may be reinforced with a braid or coil to increase its torque, flexibility, kink performance, or a combination thereof.

Tube 101 may have a desired material property. For example, tube 101 may be slidable and/or have a surface (e.g., inner lumen surface 117) that results in a low frictional value when aspirating an object therethrough), as previously described. Tube 101 may have a desired bendability or stiffness. In some instances, it may be desirable for tube 101 to be flexible and to bend to conform to changes in direction of the cavity or vasculature through which tube 101 is being navigated. Alternatively, it may be more desirable for tube 101 to be stiffer and to keep tube 101 distorting when pushing an object or catheter therethrough. In some instances, the entire tube may be stiff enough to keep from bending. Alternatively, portions of tube 101 may be stiff and portions may be flexible to permit flexing at certain predefined locations. In another example, the entirety of tube 101 may be flexible. Tube 101 can or cannot have a desired elastic property. In some embodiments, properties of tube 101 may be variable based on the morphology of tube 101. For example, tube 101 may flex or bend more easily when tube 101 is thinner, and may be stiffer when tube 101 is thicker.

Tube 101 may have a substantially uniform thickness throughout. For example, tube 101 may have a thickness of greater than, less than, or equal to about 0.02 millimeters (mm), 0.04 mm, 0.08 mm, 0.1 mm, 0.15 mm, 0.2 mm, 0.25 mm, 0.3 mm, 0.35 mm, 0.4 mm, 0.45 mm, 0.5 mm, 0.75 mm, 1 mm, 1.2 mm, 1.4 mm, 1.6 mm, 1.8 mm, 2.0 mm, 3.0 mm, 4.0 mm, or 5.0 mm. In some instances, tube 101 thickness may vary. Tube 101 thickness may vary between any degrees of thickness including measurements described herein. Tube 101 thickness may vary by greater than, less than, or equal to about 10%, 30%, 50%, 70%, 80%, 100%, 110%, 120%, 130%, 150%, 170%, 200%, 250%, 300% or 400% at two or more points along the length of tube 101. In some instances, the thickness may be greater toward a proximal portion of tube 101, or toward a distal portion of tube 101. The thickness may vary in multiple ways along the length and/or width of tube 101. For example, the thickness may increase and/or decrease once or multiple times along the length and/or width of tube 101. In some instances, the thickness of tube 101 may decrease where greater flexibility is desired. Any change in thickness may be gradual or sudden.

Referring to FIG. 1, tube coating system 100 may include seal 105, which may be coupled to tube 101 at first end 110, second end 112, or both. For example, seal 105 may be coupled to tube 101 only at second end 112. Tube 101 may be coupled to more than one seal 105. For example, tube 101 may be coupled to two seals, three seals, or four seals. In one embodiment, seal 105 is used to hermetically seal tube 101. Seal 105 may be adjustable. For example, seal 105 may be configured to fit different sized tubes and catheters. In one embodiment, seal 105 is opened and closed at various points during the process of coating inner lumen surface with a coating solution. Seal 105 may be used to couple tube 101 to withdrawal system 102.

Referring to FIG. 1, withdrawal system 102 may include means for moving coating solution 103 through tube 101. For example, withdrawal system 102 may include syringe 114 and motor 104. In some embodiments, withdrawal system 102 may include a pump or an actuating device. Withdrawal system 102 may be coupled to tube 101 to move coating solution 103 through tube 101. In one embodiment, withdrawal system 102 is coupled to tube 101 via seal 105. However, withdrawal system 102 may be coupled directly to tube 101. Syringe 114 of withdrawal system 102 may include plunger 109 and may be filled with coating solution 103. In some embodiments, coating solution 103 is stored in a reservoir or container and is moved directly through tube 101 via withdrawal system 102.

In some embodiments, withdrawal system 102 may push out and withdraw coating solution 103 at a controlled speed (or flow rate). For example, syringe 114 and plunger 109 may push out or withdraw coating solution 103 at a controlled speed (or flow rate). In some embodiments, withdrawal system 102 may push out or withdraw coating solution 103 at a controlled speed (or flow rate) that is variable. In another embodiment, withdrawal system 102 may push out or withdraw coating solution 103 at a controlled speed (or flow rate) that is fixed. In yet another embodiment, withdrawal system 102 may push out and withdraw coating solution 103 at a variable or fixed speed, and pause between pushing out and withdrawing coating solution 103 to allow additional time for coating solution 103 to adhere to inner lumen surface 117. For example, a pump or syringe 114 of withdrawal system 102 may be configured to pause between pushing out and withdrawing coating solution 103 to allow additional time for coating solution 103 to adhere to inner lumen surface 117.

A person having skill in the art will appreciate that the speed or flow rate at which coating solution 103 is moved through tube 101 will vary depending on a variety of factors, including but not limited to the type of coating solution used, the material of tube 101, and the desired thickness of coating to be deposited on inner lumen surface 117 of tube 101. In one example, a faster speed or flow rate (e.g., less contact time between coating solution 103 and tube 101 surface) may be used for coating solutions and tube materials that readily adhere together. In another example, a faster speed or slower speed (or flow rate) (e.g., less contact time between coating solution 103 and tube 101 surface or more contact time between coating solution 103 and tube 101 surface, respectively) may be desirable for applications when the thickness of coating solution 103 needs to be thicker or thinner, respectively.

Different types of coatings may be used in coating tubes of the present disclosure. Coating solution 103 may include lubricants, antimicrobial coatings, and hydrophilic surface coatings, as well as others. For instance, tube or catheter 101 may be lubricated prior to insertion in a patient. A lubricant may reduce both static and kinetic friction to ease the contact of two different surfaces. Because lubricants are used to place inorganic devices into patients' bodies, they should be both biocompatible, non-degradable, and hemocompatible (e.g., have compatibility with blood). Additionally, lubricants must avoid expansion and flaking when they come into contact with water or other fluids. In certain embodiments, an antimicrobial coating may be used to coat a surface of a tube of the present disclosure to sanitize tube 101 and prevent the transfer of external bacteria into the body environment. Hydrophilic surface coatings may also be used. Some medical devices, such as tubes, require increased wettability in order to properly function with bodily fluids and tissues. Hydrophilic surface coatings may make these medical devices susceptible to fluids (e.g., by grafting hydrophilic surface coating polymers that help to bind water onto the surface of the medical device). Non-limiting examples of coating solutions or materials that may be used in coating solution 103 include biodegradable polymers such as poly(1,8-octanediol citrate, chitosan, chitosan/poly(vinyl alcohol) blends, dermatan sulfate, dextran, hyaluronen, hyaluronic acid (HA), phosphorylcholine, poly (2-methoxyethylacrylate, polyester, polyether, Polyethylene glycol, poly-N-vinylpyrrolidone, polyurethane, Pyrolytic carbon, Sorin, stearyl poly(ethylene oxide) blends, and Trillium.

Other suitable coating solution 103 of the present disclosure are polymers or oligomers of monomers selected from ethylene oxide and its higher homologs including up to 6 carbon atoms; 2-vinyl pyridine; N-vinylpyrrolidone; polyethylene glycol acrylates such as mono-alkoxy polyethylene glycol mono(meth)acrylates, including mono-methoxy triethylene glycol mono (meth) acrylate, mono-methoxy tetraethylene glycol mono (meth) acrylate, polyethylene glycol mono (meth) acrylate; other hydrophilic acrylates such as 2-hydroxyethylmethacrylate, glycerylmethacrylate; acrylic acid and its salts; acrylamide and acrylonitrile; acrylamidomethylpropane sulfonic acid and its salts, cellulose, cellulose derivatives such as methyl cellulose ethyl cellulose, carboxymethyl cellulose, cyanoethyl cellulose, cellulose acetate, polysaccharides such as amylose, pectin, amylopectin, alginic acid, and cross-linked heparin; maleic anhydride; aldehydes; etc. These monomers may be formed into homopolymers or block or random copolymers. The use of oligomers of these monomers in coating the catheter for further polymerization is also an alternative. Preferred monomers include ethylene oxide; 2-vinyl pyridine; N-vinylpyrrolidone and acrylic acid and its salts; acrylamide and acrylonitrile each polymerized (with or without substantial cross-linking) into homopolymers, or into random or block copolymers. Additionally, hydrophobic monomers may be included in the polymeric coating material so long as the hydrophilic nature of the resulting copolymer is not substantially compromised. Suitable monomers include ethylene, propylene, styrene, styrene derivatives, alkylmethacrylates, vinylchloride, vinylidenechloride, methacrylonitrile, and vinyl acetate.

Coating solution 103 may have a viscosity of approximately 300 cps at 22 degrees Celsius. However, coating solution 103 may have a viscosity of between approximately 1 cps and approximately 300 cps at 22 degrees Celsius, between approximately 1 cps and approximately 250 cps at 22 degrees Celsius, between approximately 10 cps and approximately 150 cps at 22 degrees Celsius, greater than 300 cps at 22 degrees Celsius, or less than 1 cps at 22 degrees Celsius. In one embodiment, coating solution 103 is a hydrophilic solution. In another embodiment, coating solution 103 is a hydrophobic solution. In one embodiment, coating solution 103 is biocompatible as tube 101 may be inserted into living tissue. For example, tube 101 may be inserted into a blood vessel and coating solution 103 may be a hydrophilic polyurethane solution.

Coating solution 103 may be diluted with a dilution solution by varying the concentration of the dilution solution in order to change and specify the viscosity of coating solution 103. Specifying the viscosity of coating solution 103 improves coating performance in tube 101. Coating solution 103 may be diluted with a dilution solution by varying the percentage amount of dilution solution in coating solution 103. The percentage of coating solution 103 that is the dilution solution may be between 0% and 50%, 5-15%, 10-40%, or 20%-30%. In some examples, the percentage of coating solution 103 that is the dilution solution may be 0%, 5%, 6%, 7%, 8%, 9%, 10%, 11%, 12%, 13%, 14%, 15% 25%, 30%, 30%, 40%, 45%, or 50%. In one embodiment, the percentage of coating solution 103 that is the dilution solution is 50%, thereby substantially diluting coating solution. In another embodiment, the percentage of coating solution 103 that is the dilution solution is 10%, thereby slightly diluting coating solution 103. In one embodiment, a basecoat or primer layer or primer solution is used as an adhesion promoter to enhance the adhesion of coating solution 103 to inner lumen 115 of tube 101. The basecoat or primer may have a viscosity between approximately 1 cps and 300 cps at 25 degrees Celsius, between approximately 5 cps and 200 cps at 25 degrees Celsius, or between approximately 10 cps and 150 cps at 25 degrees Celsius. In one embodiment, the basecoat or primer has a viscosity of 1000 cps at 25 degrees Celsius.

In continued reference to FIG. 1, withdrawal system 102 may include motor 104. Motor 104 may be coupled to plunger 109 to push and withdraw coating solution 103 in and out of syringe 114. In some embodiments, withdrawal system 102 includes a pump configured to push and withdraw coating solution 103 directly in and out of tube 101. In some embodiments, coating solution 103 may be forced out of syringe 104 by motor 104 and coating solution 103 may pass through seal 105 and into tube 101. Coating solution 103 may be deposited on inner lumen surface 117 of tube 101. Motor 104 may be an electromagnetic motor such as a servo motor. However, motor 104 may be any type of motor desired. Motor 104 may be configured to push and pull plunger 109 within syringe 114. In one embodiment, motor 104 is a slow speed motor. Motor 104 may have a speed between approximately 1 mm/sec to approximately 20 mm/sec, between approximately 3 mm/sec to approximately 18 mm/sec, between approximately 5 mm/sec to approximately 10 mm/sec, less than 1 mm/sec, or greater than 20 mm/sec. For example, motor 104 may have a speed of approximately 1 mm/sec, approximately 3 mm/sec, approximately 5 mm/sec, approximately 10 mm/sec, approximately 15 mm/sec, approximately 20 mm/sec, or approximately 25 mm/sec.

In practice, tube 101 may be vertically mounted and withdrawal system 102 may be configured to drive coating solution 103 into tube 101. For example, motor 104 may be configured to push plunger 109 upwards causing coating solution 103 to enter tube 101 through seal 105. Coating solution 103 may be withdrawn from tube 101 at a slow speed by motor 104 resulting in a thin layer of coating solution 103 being deposited on inner lumen surface 117 of tube 101. For example, coating solution may be withdrawn from tube 101 at a speed of between approximately 0.8 ml/min to approximately 0.1 ml/min by motor 104 resulting in a layer between 1-14 μm thick being deposited on the inner lumen surface of tube 101. However, the speed at which coating solution 103 is withdrawn depends on the diameter of inner lumen 115 of tube 101. The speed of motor 104 may result in a surface coating rate of between approximately 5 mm/minute and approximately 10 mm/minute. However, the coating rate may be less than 5 mm/minute or greater than 10 mm/minute. For example, the coating rate may be approximately 3 mm/minute, approximately 5 mm/minute, approximately 7 mm/minute, approximately 10 mm/sec, or approximately 15 mm/minute. In some embodiments, the speed of the deposition of coating solution 103 affects various parameters of coating solution 103, such as the viscosity and thickness.

A person of skill in the art will appreciate that the speed or rate at which the coating solution is withdrawn may also be measured as a flow rate (e.g., a velocity of the liquid in mm/minute multiplied by the cross sectional area of tube 101). In one embodiment, a pressure source may be used to assist in the depositing the thin coating of coating solution 103 on the inner lumen surface of tube 101. The thin coating of coating solution 103 may be approximately 5 μm-approximately 10 μm, approximately 6 μm-approximately 9 μm, greater than 10 μm, or less than 5 μm. For example, the thin coating of coating solution 103 may be approximately 5 μm, approximately 7 μm, approximately 10 μm, or approximately 12 μm. The profile of the surface of coating solution 103 on inner lumen surface 117 may vary depending on the pressure and the withdrawal speed of coating solution 103 by motor 104. In one embodiment, tube 101 may be treated with a cleaning solution prior to deposition of coating solution 103. For example, tube 101 may be pre-treated with silanes (organic and inorganic-organic hybrids), plasma and corona plasma discharge as adhesion promoters. In another example, tube 101 may be treated with saline or an equivalent to clean inner lumen surface 117 of tube 101 prior to the application of coating solution 103.

In one embodiment, tube coating system 100 may include pressure source 116. Pressure source 116 may be coupled to tube 101. For example, pressure source 116 may be coupled to first end 110 of tube 101. Pressure source 116 may be coupled to tube 101 to allow pressure source 116 to provide pressure to the inner lumen surface of tube 101.

Pressure source 116 may generate a pressure between approximately 1 psi and approximately 4 psi, between approximately 2 psi and approximately 4 psi, between approximately 3 psi and approximately 5 psi, greater than 4 psi, or less than 1 psi. For example, pressure source 116 may generate a pressure of 1 psi, 2 psi, 3 psi, 4 psi, 5 psi, or 6 psi. In one embodiment, pressure source 116 generates a pressure between approximately 2 psi and approximately 4 psi. Pressure source 116 may be capable of generating positive pressure, negative pressure, variable pressure, or no pressure. For example, pressure source 116 may generate positive pressure to reduce the curing rate of coating solution 103. The positive pressure generated by pressure source 116 and the slow deposition of coating solution 103 by withdrawal system 102 may result in a thinner layer of coating solution 103 on inner lumen surface 117 of tube 101. For example, pressure generated by pressure source 116 and a speed of 1 mm/sec of motor 103 may result in a thin layer of 5 μm of coating solution 103 on inner lumen surface 117 of tube 101. In one embodiment, coating solution 103 is withdrawn into syringe 114 by constant head pressure applied by pressure source 116 in the same direction as the withdrawal of coating solution 103 into syringe 114. In one embodiment, coating solution 103 may be applied simultaneously to inner lumen surface 117 of tube 101 and outer surface 118 of tube 101. Further, multiple tubes may be coated with coating solution 103 simultaneously.

Figure 2:
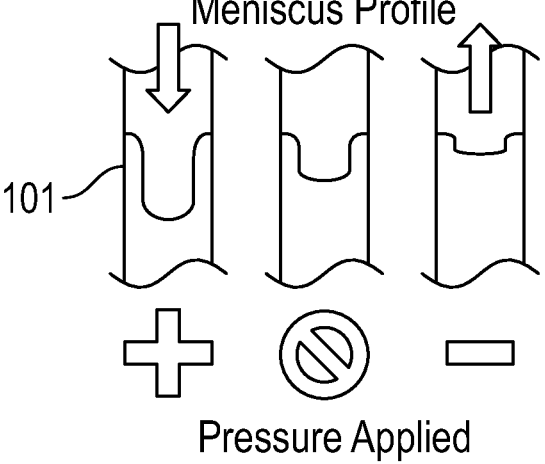
FIG. 2 is an illustration of exemplary coating meniscus profiles of an exemplary tube with varying levels of pressure in accordance with an exemplary embodiment of the present invention.

Referring to FIG. 2, different types of pressure may be applied to tube 101 via pressure source 116 to control the thickness of coating solution 103 being applied to the inner lumen surface of tube 101. For example, pressure source 116 may generate positive or negative pressures to manipulate the surface tension between coating solution 103 and inner lumen surface 117 of tube 101 to improve the application of coating solution 103 on inner lumen surface 117. For example, a positive pressure between approximately 2 psi and approximately 4 psi may be generated by pressure source 116 and may result in coating solution 103 having a thickness between, for example, approximately 1 μm to approximately 25 μm, approximately 5 μm to approximately 20 μm, or approximately 10 μm to approximately 15 μm being deposited on inner lumen surface 117 of tube 101. For example, a positive pressure between approximately 2 psi and approximately 4 psi generated by pressure source 116 may result in coating solution 103 having a thickness of approximately 1 μm, approximately 5 mm, approximately 10 μm, approximately 15 μm, approximately 20 μm, or approximately 25 μm. Pressure source 116 may generate pressure using a noble or inert gas. For example, pressure source 116 may use argon, carbon, hydrogen, oxygen, nitrogen, or any combination of those gases. In practice, the pressure generated by pressure source 116 may be constant and applied in the same direction as the withdrawal of coating solution 103 into syringe 114. In one embodiment, the profile of the meniscus of coating solution 103 is used to control and minimize coating dripping of coating solution 103 within inner lumen of tube 101 and control the thickness of coating solution 103 applied to the inner lumen surface of tube 101. The meniscus of coating solution 103 and the displacement rate of coating solution 103 may result in a non-linear relationship with the thickness of coating solution 103. In one embodiment, the positive pressure is variable and varied in accordance with the distance between the meniscus of coating solution 103 and pressure source 116.

In one embodiment, tube coating system 100 may include reservoir 119. Reservoir 119 may be coupled to syringe 114 or may be disposed between syringe 114 and seal 105.

Reservoir 119 may be polytetrafluoroethylene (PTFE) coated-polypropylene, polypropylene, or glass. Reservoir 119 may be hold a reserve of coating solution 103 and may be configured to replenish coating solution 103 within syringe 114. For example, reservoir 119 may be coupled to syringe 114 to replenish coating solution 103 that has been pushed out of syringe 114 via plunger 109 and motor 104, and deposited onto inner lumen surface 117 of tube 101. Reservoir 119 may have a capacity between capacity 10 ml and 2000 ml, 15 ml and 1800 ml, 30 ml and 1600 ml, 50 ml and 1200 ml, less than 10 ml or greater than 2000 ml. For example, reservoir 119 may have a capacity of approximately 10 ml, approximately 25 ml, approximately 50 ml, approximately 100 ml, approximately 125 ml, approximately 150 ml, approximately 200 ml, or approximately 250 ml.

In one embodiment, tube coating system 100 may include valve 120 disposed between reservoir 119 and syringe 114. For example, valve 120, which may be a luer activated valve, may be disposed between reservoir 119 and syringe 114 to control the flow of coating solution 103 from reservoir 119 to syringe 114. Valve 120 may be controlled electronically, for example, with a digital PLC, or may be controlled manually. In practice, syringe 114 may be filled with coating solution 103. Valve 120 of reservoir 119 may be closed and seal 105 may be open while motor 104 pushes plunger 109 to force coating solution 103 out of syringe 114 into tube 101. Once motor 104 may no longer push plunger 109, since there is no more coating solution 103 left in syringe 114, valve 120 of reservoir 119 may open, and seal 105 may close. When motor 104 pulls plunger 109 out of syringe 114, the negative pressure in syringe 114 results in coating solution 103 in reservoir 119 being pulled into syringe 114 since valve 120 is open and seal 105 is closed. Once syringe 114 is full of coating solution 103 and motor 104 begins again to push plunger 109, valve 120 may close, and seal 105 may open to prevent coating solution 103 from flowing back into reservoir 120, thereby allowing coating solution 103 to flow into tube 101.

In one embodiment, after coating solution 103 has been deposited on inner lumen surface 117 of tube 101, coating solution 103 may be cured to increase adherence to inner lumen surface 117 of tube 101. For example, coating solution 103 may be heat cured in, for example, an oven after it has been deposited on inner lumen surface 117 of tube 101. In one embodiment, coating solution 103 is heat cured at a temperature between 20 degrees Celsius and 90 degrees Celsius, 30 degrees Celsius and 100 degrees Celsius, 50 degrees Celsius and 80 degrees Celsius, or greater than 90 degrees Celsius for a duration of 10 minutes to 480 minutes (8 hours). For example, coating solution 103 may be heat cured at a temperature of 20 degrees Celsius, 30 degrees Celsius, 40 degrees Celsius, 50 degrees Celsius, 60 degrees Celsius, 70 degrees Celsius, 80 degrees Celsius, 90 degrees Celsius, or 110 degrees Celsius for a duration between 10 minutes and 480 minutes (8 hours). In one embodiment, coating solution 103 is heat cured at between room temperature and 90 degrees Celsius. For example, coating solution 103 may be heat cured between approximately 20 degrees Celsius and approximately 90 degrees Celsius. However, coating solution 103 may be cured at a temperature as high as 150 degrees Celsius. In another embodiment, coating solution 103 may be cured using ultraviolet (UV) light. For example, coating solution 103 may be mixed with a UV-curing agent in order to assist in curing coating solution 103 with UV light.

In one embodiment, subsequent coating solutions may be used after coating solution 103 to coat the inner lumen surface of tube 101. The use of an adhesion promotor may be used to vary the wetting profile of the inner lumen surface of tube 101. This may improve the adhesion of coatings subsequent to the application of coating solution 103 within tube 101.

Applications

In some embodiments, coating solution 103 may be used to coat an inner surface of a catheter to reduce and minimize friction within the catheter. For example, coating solution 103 may be used with a balloon occlusion catheter to coat on inner surface of an outer tube, thereby reducing friction between the inner tube and the outer tube. Coating solution 103 may be used with other catheters to reduce friction between embolic particles or coils, medicament or particles traveling within catheter and the inner surface of the catheter. Using coating solution 103 allows catheters to be made out of materials that may be thermoset, allowing them to be shaped, which is not possible with certain low-friction materials, such as PTFE.

Figure 3A:
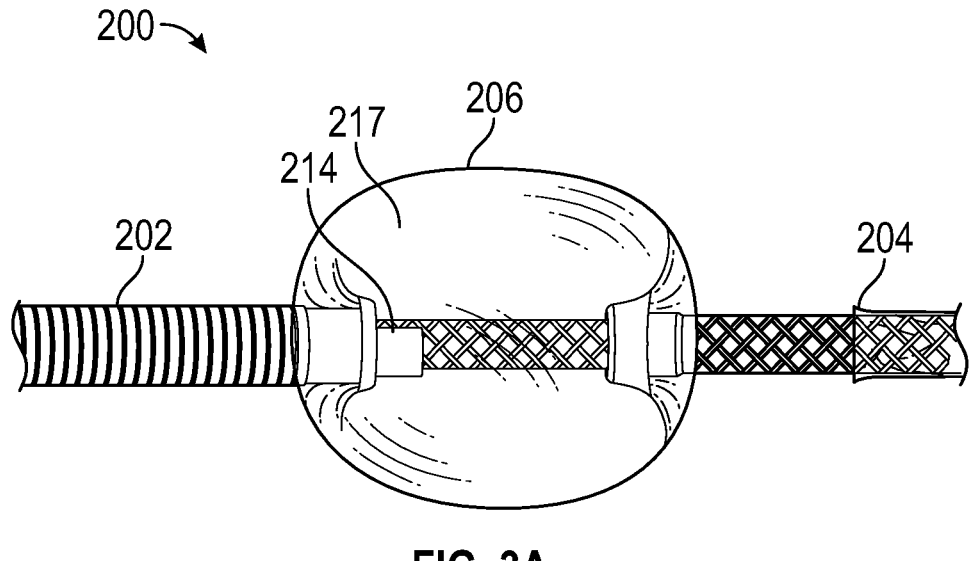
FIG. 3A is a side view of an exemplary balloon catheter in accordance with an exemplary embodiment of the present invention shown with the balloon in an inflated state.
Figure 3B:
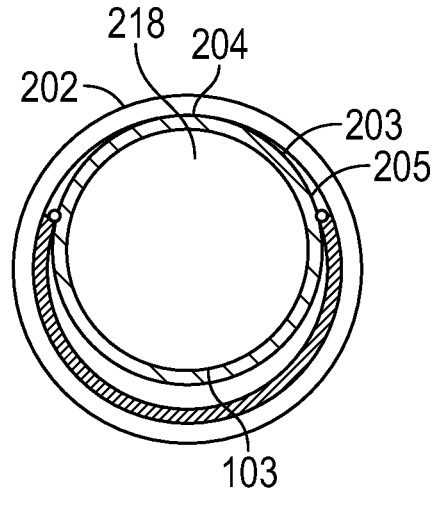
FIG. 3B is a cross sectional side view of the collar of FIG. 3A shown with the balloon removed.

Referring to FIGS. 3A and 3B, coating solution 103 may be used with catheter 200, which may be a balloon catheter. Catheter 200 may be configured to deliver fluid and/or particles to a target site, occlude a blood vessel, dilate a blood vessel, access the interior of an organ or vessel, and/or deliver a therapeutic agent. Catheter 200 may include outer tube 202, inner tube 204, and balloon 206. Outer tube 202 may house inner tube 204, such that inner tube 204 is at least partially disposed within outer tube 202. Inner tube 204 may be similar to tube 101. Inner tube 204 may include inner lumen 218, which may be sized to deliver particles and/or objects to a target area. For example, the diameter of inner lumen 218 of inner tube 204 may be sized to house and deliver contrast, embolic particles or coils, medicament or particles to a target site, and/or surgical tools. Catheter 200 may further include balloon 206, which may be coupled to catheter 200. Balloon 206 may have a proximal end and a distal end. The proximal end of balloon 206 may be coupled to outer tube 102 or another element of catheter 200, and the distal end may be coupled to inner tube 204. Balloon 206 may be configured to inflate and deflate. When inflated, balloon 206 may include interior space 217.

Catheter 200 may include coating solution 103. Coating solution 103 may be deposited within inner lumen 218 of inner tube 204. Coating solution 103 may be configured to decrease the friction of particles, catheters, implants, medicaments, tools, or any other object within inner lumen 218. For example, coating solution 103 may be used to deliver compressible embolic particles to a target site with minimal friction between the particles and inner lumen 218. In some embodiments, coating solution 103 may also be configured to decrease the friction between inner surface 203 of outer tube 202 and outer surface 205 of inner tube 204 when inner tube 204 is disposed within outer tube 202.

Figure 4:
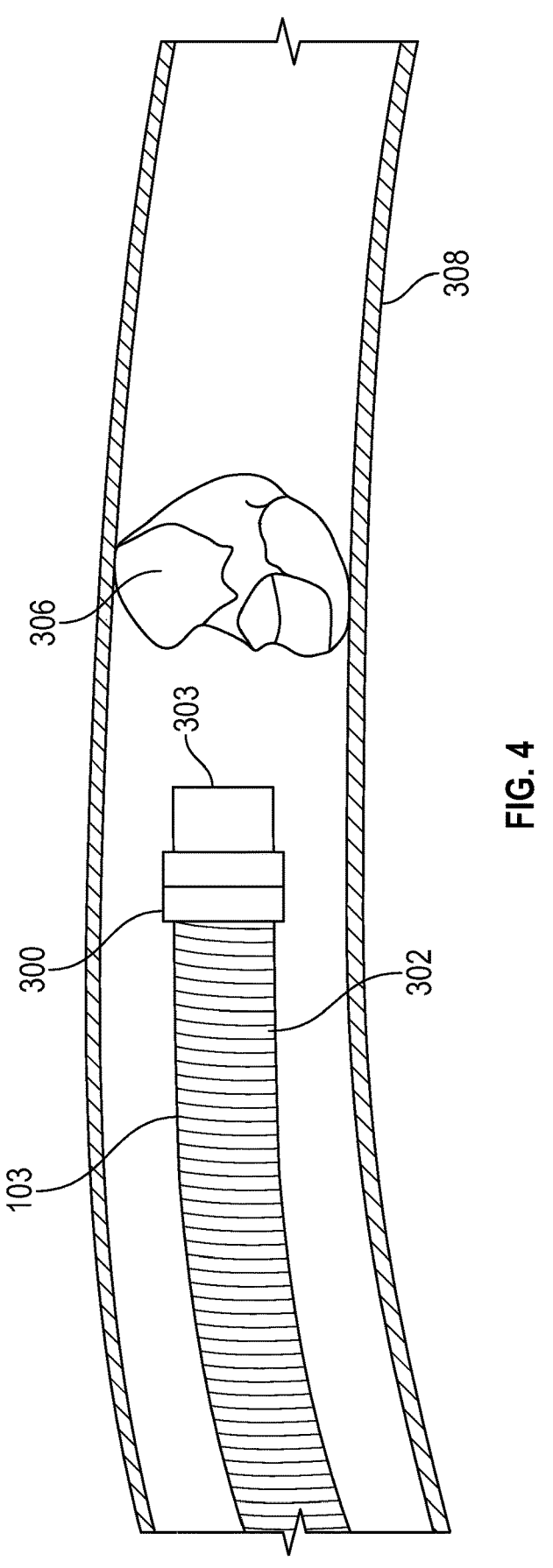
FIG. 4 is an illustration of an exemplary catheter in accordance with an exemplary embodiment of the present invention.

Referring to FIG. 4, coating solution 103 may be used with a catheter 300 to remove objects from within lumen 308. Catheter 300 may include inner surface 302 and opening 303, and may be configured to be used with a vacuum source to aspirate object 306. A pressure or vacuum may be applied within the interior of catheter 300 resulting in object 306, located adjacent to opening 303, being sucked into catheter 300. In some embodiments, lumen 308 may be a blood vessel. However, lumen 308 may be any type of lumen, such as, for example, a gastrointestinal tract or an airway.

In some embodiment, object 306 may be an obstruction, a particle, a coil, a medicament, a tumor, a tool, a device, or any other object that may be disposed within lumen 308. Once opening 303 is adjacent to object 306, a vacuum may be applied to catheter 300 to suck object 306 into catheter 300. Object 306 may be sucked into catheter 300 in its entirety since partitioning and breaking up of object 306 may be dangerous, especially if object 306 is a clot or tumor. For example, if object 306 is a clot or tumor, partitioning and breaking up of the clot may result in portions of the clot remaining within the blood vessel. Therefore, in some embodiments, object 306 must travel down catheter 300 and engage with inner surface 302 without breaking apart. However, in some embodiments, object 306 may be broken up if it is too large to fit through opening 303 of catheter 300. In some embodiments, object 306 travelling down catheter 300 results in significant contact between object 306 and inner surface 302.

In some embodiments, coating solution 103 may be disposed on inner surface 302 to reduce the friction between object 306 and inner surface 302, allowing object 306 to easily travel down catheter 300. For example, coating solution 103 may be used on inner surface 302 to ensure that object 306 does not break up or partition while traveling within catheter 300. Coating solution 103 may be deposited on inner surface 302 prior to insertion of catheter 300 into lumen 308. Coating solution will also serve to reduce the force needed to move 306 or any catheter through the catheter 300

Figure 5A:
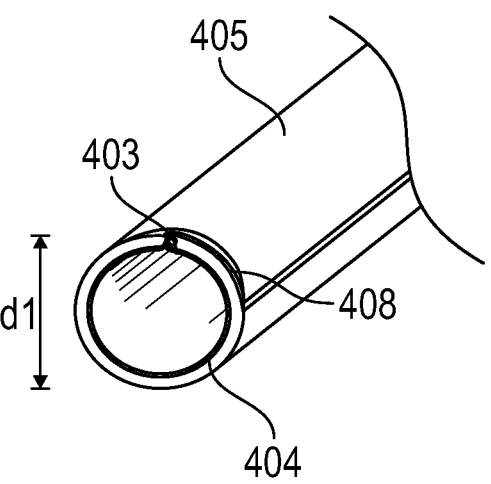
FIG. 5A is an illustration of an exemplary expandable tube in accordance with an exemplary embodiment of the present invention shown in a folded state.
Figure 5B:
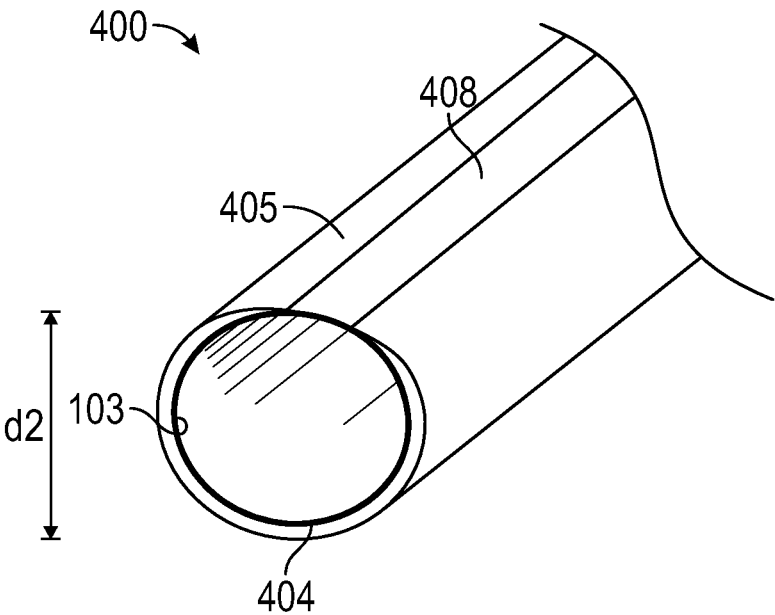
FIG. 5B is an illustration of the exemplary expandable tube of FIG. 5A shown in an expanded state.

Referring to FIGS. 5A and 5B, coating solution 103 may be used with expandable tube 400. Expandable tube 400 may be configured to be in a folded state (FIG. 5A) and an expanded state (FIG. 5B). Expandable tube 400 may include outer shell 405 and inner shell 403. Inner shell 403 may be flexible and may include inner surface 404. Inner shell 403 may be comprised of low friction material, such as PTFE. Outer shell 405 may be comprised of high strength material, such as high-density polyethylene (HDPE), Nylon, or Pebax. Expandable tube 400 may include expansion portion 408, which includes a portion of inner shell 403. Expandable portion 408 may be exposed when expandable tube 400 is in an expanded state (FIG. 5B) and folded or collapsed when expandable tube 400 is a folded or collapsed state (FIG. 5A). Expandable tube 400 may have diameter d1 in a folded or collapsed state and diameter d2 in an expanded state. In an expanded state, diameter d2 may be larger than diameter d1.

Expansion portion 408 may be configured to fold such that expansion portion 408 folds onto a portion of outer shell 405. As shown in FIG. 5A, when expansion portion 408 folds over onto a portion of outer shell 405, expandable tube 400 is in a folded state. As shown in FIG. 5B, when expansion portion 408 expands outward such that expansion portion 408 unfolds, expandable tube 400 is an expanded state. Expandable tube 400 may be configured to expand to increase its diameter from diameter d1 to diameter d2. Expandable tube 400 may be at diameter d1 (FIG. 5A) when it is inserted into a lumen and may expand to diameter d2 (FIG. 5B) once an object is passing through. In some embodiments, expandable tube 400 returns back to a folded or compressed state (FIG. 5A) after the object has passed through expandable tube 400. For example, the mere presence of an object within expandable tube 400 may be result in expandable tube 400 being in an expanded state. Once the object is no longer in expandable tube 400, expandable tube may return to a folded state. In some embodiments, expandable tube 400 is biased to be in a folded state. For example, expandable portion 408 may include elastic material that is configured to bias expandable portion 408 in a folded state.

In some embodiments, expandable tube 400 may expand when an object enters inner shell 403 that is larger than diameter d1. An object that is larger than d1 entering expandable tube 400 may cause expansion portion 408 to unfold, thereby increasing the diameter of expandable tube 400 from diameter d1 to diameter d2. The unfolding of expansion portion 408 allows expandable tube 400 to deliver an object, particle, coil, catheter, device, or tool that is larger than diameter d1. For example, expandable tube 400 may be in a folded state when entering a lumen. Once an object larger than diameter d1 enters lumen, expandable sheath 400 expands to an expanded state (FIG. 5B) by expansion portion 408 unfolding, thereby increasing the diameter of catheter 400 from diameter d1 to diameter d2. In an alternative embodiment, expansion portion 408 may be configured to expand and contract, instead of fold and unfold. Expansion portion 408 may be comprised of a flexible material and may be biased to be in a relaxed, unexpanded, state. In the relaxed state, expandable tube 400 may have diameter d1. When an object is within expandable tube 400, expansion portion 408 may stretch and expand such that expandable tube is enlarged to have diameter d2. Once the object is no longer within expandable tube 400, expansion portion 408 may be biased to retract to the relaxed state.

Since the presence of an object results in expandable tube 400 entering an expanded state, via unfolding or stretching, the maximum diameter of the object may be similar to the diameter of expandable tube 400 when the object is in expandable tube 400. This may result in increased friction between inner surface 404 and the object within expandable tube 400 due to the lack of free space between inner surface 404 and the object. Coating solution 103 may be disposed on inner surface 404 to reduce the friction between the object being delivered and inner surface 404.

Figure 6:
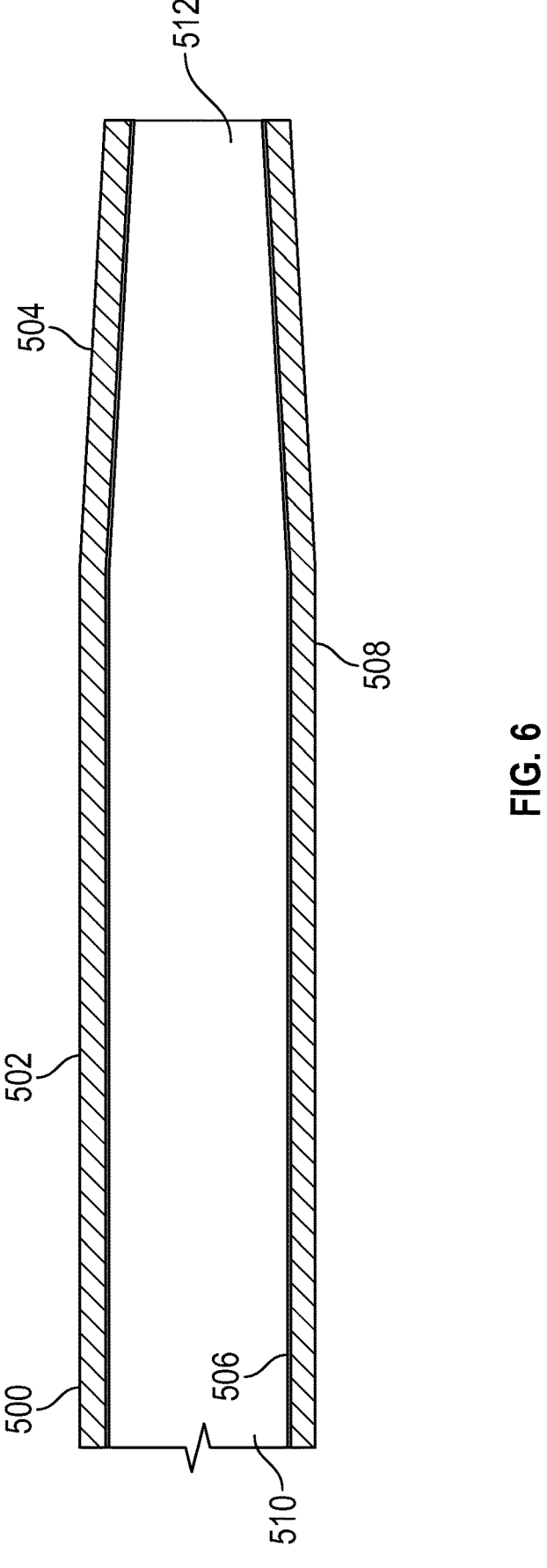
FIG. 6 is an illustration of an exemplary catheter having a tapered sheath in accordance with an exemplary embodiment of the present invention.

Referring to FIG. 6, coating solution 103 may be used with tapered sheath 500. Tapered sheath 500 may include shaft 502, tip 504, outer jacket 506, inner surface 508, proximal opening 510, and distal opening 512. Tapered sheath 500 may have a homogeneous material along its length. Shaft 502 may comprise a majority of tapered sheath 500 and may be proximate to proximal opening 510. Tip 504 may be proximate distal opening 512 and distal opening 512 may have a diameter smaller than the diameter of proximal opening 510. In one embodiment, outer jacket 506 is comprised of a thermoplastic material and inner surface 508 is comprised of a thermoplastic material lined with coating solution 103. Tapered sheath 500 may be tapered for the length of tip 504 towards distal opening 512. However, tapered sheath 500 may be tapered anywhere. For example, tapered sheath 500 may be tapered at shaft 502 or may be tapered only at tip 504. Tapered sheath 500 may be tapered to minimize clearance between a device inserted into tapered sheath 500 and distal opening 512. Tip 504 may be the last 5 to 15 mm of tapered sheath 500. The tapering of tapered sheath 500 may be enabled by using a thermoplastic material, which may be reflowed into a new shape or taper. Coating solution 103 may be disposed within tapered sheath 500 to reduce the friction of inner surface 506 and the device being inserted into tapered sheath 500.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a," "an" and "the" are not limited to one element but instead should be read as meaning "at least one."

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

What is claimed is:

1. A method for coating an inner lumen surface of a tube with a coating solution comprising the steps of: moving a coating solution through a tube from a second end of the tube toward a first end of the tube opposite the second end via a withdrawal system disposed at the second end and depositing the coating solution onto an inner lumen surface of the tube, wherein a thickness of the coating solution being deposited onto the inner lumen surface of the tube is between 1 um and 25 um;

applying a first pressure to the tube using a pressure source disposed at the first end when the coating solution is within the tube to manipulate a profile of a meniscus of the coating solution to control the thickness of the coating solution being applied to the inner lumen surface of the tube; and withdrawing the coating solution from the tube at a controlled flow rate via the withdrawal system, the withdrawal system applying a second pressure simultaneously to and independently of the first pressure applied by the pressure source.

2. The method of claim 1 further comprising:

preparing the inner lumen surface of the tube for application of the coating solution using a cleaning solution.

3. The method of claim 2, wherein the cleaning solution is saline or an equivalent.

4. The method of claim 2, wherein the inner lumen surface is pre-treated with one or more of silanes, plasma, and corona plasma discharge, the one or more of silanes, plasma, or corona plasma acting as an adhesion promoter.

5. The method of claim 1, wherein a ratio between an inner diameter of the tube and a length of the tube is between 1:100 and 1:4000.

6. The method of claim 1, wherein the withdrawal system includes a syringe and plunger.

7. The method of claim 1, wherein the withdrawal system includes a pump.

8. The method of claim 1, wherein the first pressure being applied to the tube by the pressure source is positive pressure.

9. The method of claim 1, wherein the first pressure being applied to the tube by the pressure source is negative pressure.

10. The method of claim 1 further comprising:

upon the coating solution being deposited on the inner lumen surface, curing the coating solution such that it adheres to the inner lumen surface of the tube.

11. The method of claim 10, wherein the coating solution is heat cured between 20 degrees Celsius and 90 degrees Celsius.

12. The method of claim 10, wherein the coating solution is heat cured for a duration of between 10 minutes and 8 hours.

13. The method of claim 10, wherein the coating solution is cured using ultraviolet light.

14. The method of claim 1, wherein the coating solution is a hydrophilic coating.

15. The method of claim 1, wherein the coating solution is a hydrophobic coating.

16. The method of claim 1, where the coating solution is diluted with a dilution solution by varying a concentration of the dilution solution to change the thickness of the coating solution.

17. The method of claim 1 further comprising:

applying a primer solution or a basecoat solution between the inner lumen surface of the tube and the coating solution, wherein the primer solution or the basecoat solution is used as an adhesion promoter.

18. The method of claim 1 further comprising:

simultaneously applying the coating solution to the inner lumen surface of the tube and an outer surface of the tube.

19. The method of claim 1, wherein multiple inner lumens of multiple tubes are coated simultaneously.

20. A method for coating an inner lumen surface of a tube with a coating solution comprising the steps of:

moving a coating solution through a tube from a second end of the tube toward a first end of the tube opposite the second end via a withdrawal system disposed at the second end and depositing the coating solution onto an inner lumen surface of the tube, wherein a thickness of the coating solution being deposited onto the inner lumen surface of the tube is between 1 um and 25 um, wherein the withdrawal system includes a pump;

applying a positive pressure to the tube using a pressure source disposed at the first end when the coating solution is within the tube to manipulate a profile of a meniscus of the coating solution to control the thickness of the coating solution being applied to the inner lumen surface of the tube;

withdrawing the coating solution from the tube at a controlled flow rate via the withdrawal system, the withdrawal system applying a second pressure simultaneously to and independently of the positive pressure applied by the pressure source; and curing the coating solution such that it adheres to the inner lumen surface of the tube, wherein the coating solution is heat cured between 20 degrees Celsius and 90 degrees Celsius.

21. The method of claim 1, wherein the coating solution is a lubricant having a coefficient of friction less than 0.2 to reduce friction between the inner lumen surface and an object disposed within the tube when the coating solution is deposited on the inner lumen surface.

22. The method of claim 21, wherein the coefficient of friction less than 0.1.

23. The method of claim 20, wherein the coating solution is a lubricant having a coefficient of friction less than 0.2 to reduce friction between the inner lumen surface and an object disposed within the tube when the coating solution is deposited on the inner lumen surface.

\* \* \* \* \*